United States Patent [19]
Lawandy

[11] Patent Number: 5,881,886
[45] Date of Patent: Mar. 16, 1999

[54] OPTICALLY-BASED METHODS AND APPARATUS FOR SORTING GARMENTS AND OTHER TEXTILES

[75] Inventor: Nabil M Lawandy, North Kingston, R.I.

[73] Assignee: Brown University Research Foundation, Providence, R.I.

[21] Appl. No.: 842,716

[22] Filed: Apr. 16, 1997

Related U.S. Application Data

[60] Continuation-in-part of Ser. No. 401,356, Mar. 9, 1995, Pat. No. 5,625,456, which is a division of Ser. No. 210,710, Mar. 18, 1994, Pat. No. 5,448,582.

[51] Int. Cl.$^6$ .................................................. B07C 5/02
[52] U.S. Cl. ........................... 209/3.3; 209/579; 209/583
[58] Field of Search .................... 209/3.3, 579, 576, 209/577, 583; 372/39, 42, 54, 53, 6

[56] References Cited

U.S. PATENT DOCUMENTS

| | | | |
|---|---|---|---|
| 3,313,941 | 4/1967 | Marks | 250/219 |
| 4,036,365 | 7/1977 | Rosenfeld | 209/73 |
| 4,301,426 | 11/1981 | Schneider | 331/94.5 |
| 4,519,082 | 5/1985 | Schneider | 372/42 |
| 4,672,619 | 6/1987 | Luty et al. | 372/42 |
| 4,767,205 | 8/1988 | Schwartertel | 356/71 |
| 4,857,784 | 8/1989 | Takiguchi | 356/76 X |
| 4,878,224 | 10/1989 | Kuder et al. | 372/53 |
| 4,964,133 | 10/1990 | Pollock et al. | 372/42 |
| 5,023,139 | 6/1991 | Birnboim et al. | 428/402 |
| 5,157,674 | 10/1992 | Lawandy | 372/22 |
| 5,233,621 | 8/1993 | Lawandy | 372/22 |
| 5,237,582 | 8/1993 | Moses | 372/53 |
| 5,253,258 | 10/1993 | Lawandy | 372/22 |
| 5,422,489 | 6/1995 | Bhargava | 250/488.1 |
| 5,434,878 | 7/1995 | Lawandy | 372/43 |

FOREIGN PATENT DOCUMENTS 63 233592(A) 9/1988 Japan .

OTHER PUBLICATIONS

"Non–Resonant Feedback in Lasers" by R. V, Ambartsumyan, N. G. Basov, P.G. Kryukov and V. S. Letokhov, Science Library, copyright 1970.

"Brillouin and Rayleigh S Cathering in Aprotic Scattering in Aprotic Laser Solutions Containing Neodymium" by R. Pappalardo and A. Lempicki, Jrnl. Appl. Phys. vol., 43, No. 4, Apr. 1972, pp. 1699–1708.

"Airbourne Laser Radar for Mapping Two–Dimensional Contours of Aerosol Concentration" by G.W. Grams, E. M. Patterson and C.M. Wyman, Optical and Quantum Electronics, No. 3, May 1975, pp. 187–191.

(List continued on next page.)

*Primary Examiner*—David H. Bollinger
*Attorney, Agent, or Firm*—Perman & Green, LLP

[57] ABSTRACT

A method is disclosed for sorting textiles, as is a system that operates in accordance with the method. The method includes steps of (a) providing a plurality of textiles to be sorted, each of the textiles comprising a portion that includes an electromagnetic radiation emitting and amplifying material; for each textile, (b) illuminating at least the portion with laser light that exceeds a threshold fluence; (c) detecting a narrow band laser-like emission of at least one wavelength from the portion in response to the step of illuminating; and (d) sorting the textiles based on the detected laser-like emission. In one embodiment the textile has at least one stitched-in thread, the thread comprising a substrate material and the electromagnetic radiation emitting and amplifying material in combination with scatterers for providing the laser-like emission. In another embodiment the textile has an applied patch containing the electromagnetic radiation emitting and amplifying material. In this case the scatterers can comprise the material of the textile either alone or in combination with the material of the patch. The emission wavelength(s) are selected so as to encode desired information, such as a customer identification, a date the textile was first placed into service, an identification of the vendor of the textile, an identification of the type and/or size of the textile, etc.

47 Claims, 8 Drawing Sheets

OTHER PUBLICATIONS

"Synthesis and Characterization of Nearly Monodisperse CdE (E=, Se, Te) Semiconductor Nanocrystallites" by C.B. Murray, D.M. Norris, and M.G. Bawendi, Jrnl. Am. Chem. Soc. 1993, 115, Mar. 22, 1993, pp. 8706–8715.

"Stimulated Emission of an Ensemble of Scattering Particles with Negative Absorption", by V.S. Letokhov, USSR Academy of Science, 10 Feb. 1967.

"Transmission Losses in Aprotic Liquid Lasers", C. Brecher, K. French, W. Watson, and D. Miller, Jrnl. of Applied Physics, vol. 41, No. 11, Oct. 1970, pp. 4578–4581.

"Laser Liquid", Sylvania Precision Materials, Towanda, PA (Temporary Data Sheet), Jun. 3, 1970.

"Generation of Light by a Scattering Medium with Negative Resonance absorption", Sov. Phys. JETP. vol. 26, No. 4, Apr. 1968, pp. 835–839.

"Generation of Simulated Noncoherent Radiation in Light–Scattering Media Exhibiting Chemical Reactions", Sov. J. Quantum Electron, 12(5), May 1982, pp. 588–594.

"Optical Properties of Manganese–Doped Nanocrystals of ZnS", in the American Physical Society, vol. 72, No. 3, Jan. 19, 1994, by R. N. Bhargava and D. Gallagher.

"Doped Nanocrystals of Semiconductor–A New Class of Luniescent Materials" 1993 International Conference on Luninescence, THIB–2, Aug. 9–13, 1993, Univ. of Conn. by R. N. Bhargava.

"Photonic textile fibers", R. M. Balachandran et al., Applied Optics, vol. 35, No. 12, Apr. 20, 1996, pp. 1991–1994.

OPTICALLY-BASED METHODS AND APPARATUS FOR SORTING GARMENTS AND OTHER TEXTILES

CROSS-REFERENCE TO A RELATED PATENT APPLICATION

This patent application is a continuation-in-part of U.S. patent application Ser. No. 08/401,356, filed Mar. 9, 1995, now U.S. Pat. No. 5,625,456, issued on Apr. 29, 1997, which is a divisional patent application of U.S. patent application Ser. No. 08/210,710, filed Mar. 18, 1994, entitled "Optical Sources Having a Strongly Scattering Gain Medium Providing Laser-Like Action", by Nabil M. Lawandy, now U.S. Pat. No. 5,448,582, issued Sep. 5, 1995.

FIELD OF THE INVENTION

This invention relates generally to optically-based methods and apparatus for sorting garments and other textiles.

BACKGROUND OF THE INVENTION

In U.S. Pat. No. 5,448,582, issued Sep. 5, 1995, entitled "Optical Sources Having a Strongly Scattering Gain Medium Providing Laser-Like Action", the inventor disclosed a multi-phase gain medium including an emission phase (such as dye molecules) and a scattering phase (such as $TiO_2$). A third, matrix phase may also be provided in some embodiments. Suitable materials for the matrix phase include solvents, glasses and polymers. The gain medium is shown to provide a laser-like spectral linewidth collapse above a certain pump pulse energy. The gain medium is disclosed to be suitable for encoding objects with multiple-wavelength codes, and to be suitable for use with a number of substrate materials, including polymers and textiles.

A problem exists in the field of sorting garments and textiles, such as rented work uniforms, sheets, towels, surgical covers and wraps, and similar materials. For example, it may be desirable to mass wash and press a large number of rented shirts, and then to sort the shirts for delivery to a number of different customers. If the shirts are marked with a customer-identifying indicia, such as lettering and/or a bar code, using an ink, after several washings the indicia may become unreadable to human or optically based scanners. Also, it may be difficult to properly align the indicia with an optical reader, thus impairing the recognition accuracy. This is especially true when the garments are moving relative to the scanner, such as when they are attached to a moving rail or placed on a conveyor belt. In such an application an output of the reader, such as a bar code scanner, can be used to operate a mechanical diverter, so as to route the sorted garments to different locations. If the recognition accuracy is not optimum the end result is incorrectly sorted garments.

This problem is even more pronounced if soiled garments or textiles are to be scanned, sorted and/or accounted for when returned by customers. The presence of dirt, grease, and other materials may obscure the indicia, making accurate recognition even more problematical.

OBJECTS OF THE INVENTION

It is thus a first object of this invention to provide an improved method and apparatus for sorting garments and textiles.

It is a further object of this invention to provide improved optically-based methods and apparatus for sorting garments and textiles.

It is another object of this invention to provide a substrate or patch that can be permanently affixed to a garment or textile, the substrate including an optical gain medium that when excited by an optical source emits light having at least one predetermined emission wavelength that can be optically detected.

It is a further object of this invention to provide a thread that can be permanently affixed to a garment or textile such as by stitching, the thread including an optical gain medium that when excited by an optical source emits light having at least one predetermined emission wavelength that can be optically detected.

SUMMARY OF THE INVENTION

The foregoing and other problems are overcome and the objects of the invention are realized by methods and apparatus in accordance with embodiments of this invention.

A method is disclosed for sorting textiles, as is a system that operates in accordance with the method. The method includes steps of (a) providing a plurality of textiles to be sorted, each of the textiles comprising a portion that includes an electromagnetic radiation emitting and amplifying material; for each textile, (b) illuminating at least the portion with laser light that exceeds a threshold fluence; (c) detecting a narrow band laser-like emission of at least one wavelength from the portion in response to the step of illuminating; and (d) sorting the textiles based on the detected laser-like emission.

In one embodiment the textile has at least one stitched-in thread, the thread comprising a substrate material and the electromagnetic radiation emitting and amplifying material in combination with scatterers for providing the laser-like emission in response to the step of illuminating. The scatterers comprise the material of the textile either alone or in combination with scattering particles added to the thread.

In another embodiment the textile has an applied patch containing the electromagnetic radiation emitting and amplifying material in combination with scatterers for providing the laser-like emission in response to the step of illuminating. In this case the scatterers comprise the material of the textile either alone or in combination with the material of the patch. The patch is preferably applied such that the electromagnetic radiation emitting and amplifying material is interposed between an exposed surface of the patch and a surface of the textile. The electromagnetic radiation emitting and amplifying material is preferably comprised of at least one of a dye or a phosphor.

The electromagnetic radiation emitting and amplifying material is selected to wavelength encode information regarding the textile. By example, the emission wavelength or wavelengths are selected so as to encode desired information, such as a customer identification, a date the textile was first placed into service, an identification of the vendor of the textile, an identification of the type and/or size of the textile, etc.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

The disclosure of the above-referenced U.S. Pat. No. 5,448,582, issued Sep. 5, 1995, entitled "Optical Sources Having a Strongly Scattering Gain Medium Providing Laser-Like Action", by Nabil M. Lawandy is incorporated by reference herein in its entirety. Also incorporated by reference herein in its entirety is the disclosure of U.S. Pat. No. 5,434,878, issued Jul. 18, 1995, entitled "Optical Gain Medium Having Doped Nanocrystals of Semiconductors and also Optical Scatterers", by Nabil M. Lawandy.

This invention employs an optical gain medium that is capable of exhibiting laser-like activity when excited by a source of excitation energy, as disclosed in the above-referenced U.S. Patents. The optical gain medium is comprised of: a matrix phase, for example a polymer or solvent, that is substantially transparent at wavelengths of interest; an electromagnetic radiation emitting and amplifying phase, for example a chromic dye or a phosphor; and a high index of refraction contrast electromagnetic radiation scattering phase, such as particles of an oxide and/or scattering centers within the matrix phase.

This invention employs the discovery by the inventor that a dye or some other material capable of emitting light, in combination with scattering particles or sites, exhibits electro-optic properties consistent with laser action; i.e., a laser-like emission that exhibits both a spectral linewidth collapse and a temporal collapse at an input pump energy above a threshold level.

The invention is applied herein to the identification and sorting of garments and textiles. Those skilled in the art will recognize that the teaching of this invention can be employed in a large number of sorting and identification applications.

Figure 1:
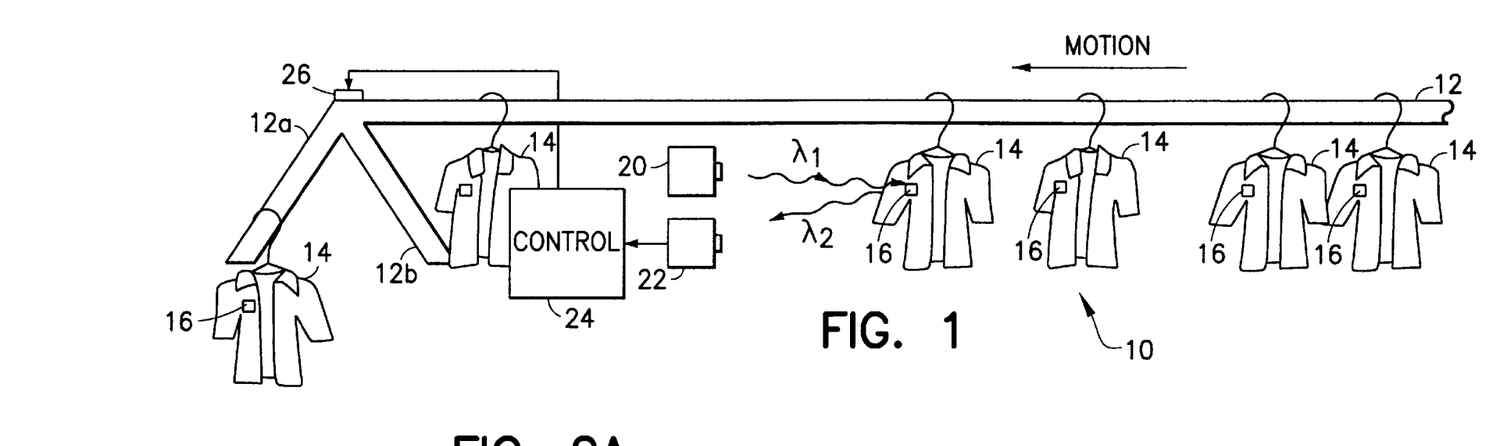
FIG. 1 illustrates a garment sorting system that is constructed and operated in accordance with this invention.

FIG. 1 illustrates an exemplary garment sorting system 10 that is constructed and operated in accordance with this invention. A moving rail or conveyor 12 is used to convey textiles such as garments 14 (e.g., shirts) past a laser 20 and a photodetector 22. Each garment 14 is provided, in accordance with this embodiment of the invention, with a label, tag, or patch 16 that is affixed to the garment by sewing, by heat, or with an adhesive.

Figure 2A:
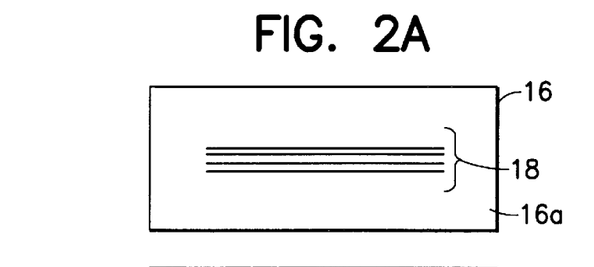
FIG. 2A is a view of one surface of a garment patch having a plurality of linear regions on or within the surface, each of the linear regions comprising an optical gain medium.
Figure 2B:
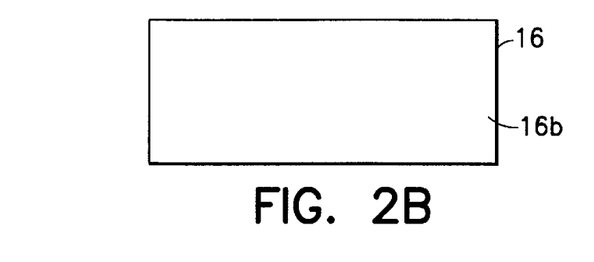
FIG. 2B is a view of an opposite surface of the patch of FIG. 2A.
Figure 6:
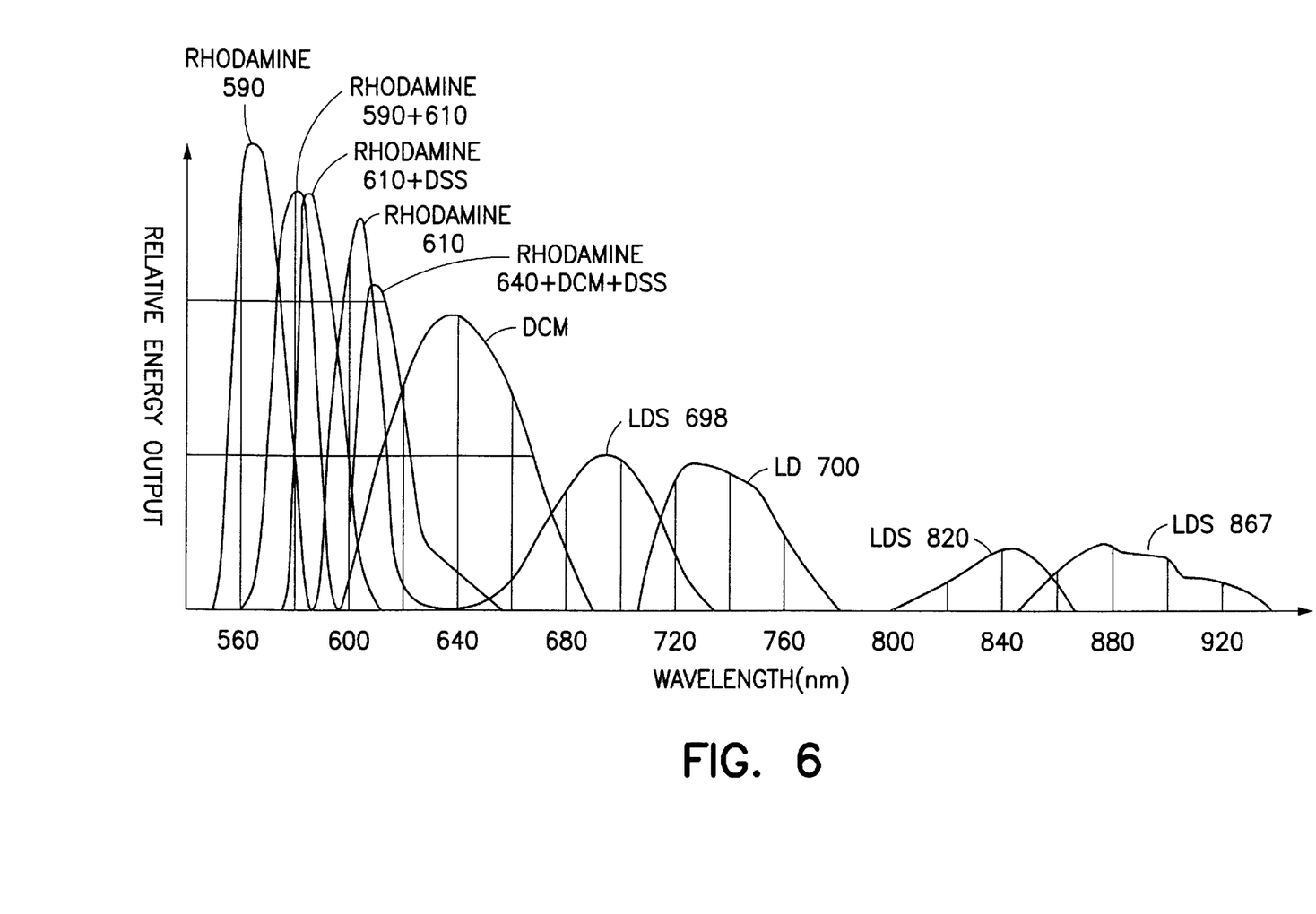
FIG. 6 is a graph illustrating the emission wavelengths of a plurality of dyes.

FIG. 2A is a view of one surface 16a of a patch 16 having a plurality of linear regions 18 located on or within the surface 16a, each of the linear regions comprising a dye forming an electromagnetic radiation emitting and amplifying phase. FIG. 2B is a view of an opposite surface 16b of the patch of FIG. 2A. The patch 16 may be comprised of a flexible nylon-based material, cotton, or any material that is suitable for being affixed to a garment or textile. Although four linear regions 18 are illustrated, a given patch may have more or less than four linear regions. Each linear region 18 includes one dye selected from N different dyes, each capable of emitting a characteristic wavelength. FIG. 6 illustrates a number of suitable dyes and their respective emission wavelengths plotted against relative energy output. The teaching of this invention is not limited for use with only the dyes listed in FIG. 6.

Figure 3:
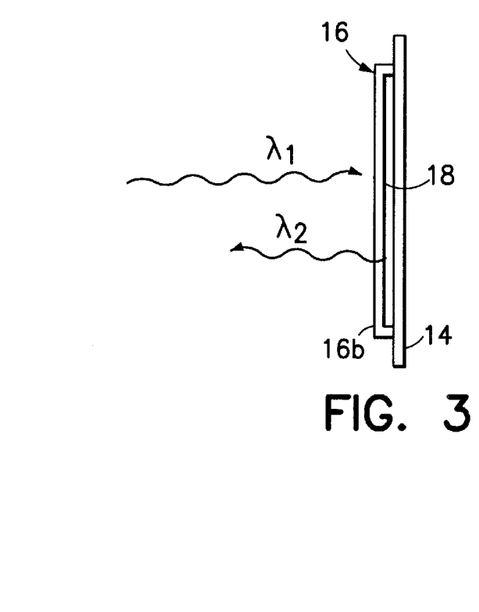
FIG. 3 is a cross-sectional view of the tag of FIGS. 2A and 2B when affixed to a garment.

FIG. 3 is a cross-sectional view of the patch 16 of FIGS. 2A and 2B when affixed to the garment 14. As can be seen, the surface 16b faces away from the surface of the garment 14, resulting in the linear regions 18 being interposed between the surface of the garment and the surface 16b of the patch 16. When excited with light having a wavelength $\lambda_1$ each of the linear regions emits with its characteristic wavelength $\lambda_2$. Due to the relative thinness of the patch (e.g., a few hundred micrometers) the excitation light and the emission light are both capable of passing though the patch 16.

In accordance with an aspect of this invention the combination of the patch 16, garment 14, and interposed linear regions 18 forms an optical gain medium capable of temporal and spectral collapse. That is, the material of the patch 16 and garment 14, which surround the linear regions 18, form the scattering/matrix phases. Light emitted from the regions 18 is scattered by the patch/garment combination, and the combination provides a laser-like emission as described in the above-referenced U.S. Pat. No. 5,448,582. That is, the combination of the regions 18 and the surrounding patch/garment exhibits electro-optic properties consistent with laser action; i.e., an output emission that exhibits both a spectral linewidth collapse and a temporal collapse at an input pump energy above a threshold level, as described in U.S. Pat. No. 5,448,582. The thickness of the patch 16 is preferably about two scattering lengths of the emitted electromagnetic radiation within the material of the patch.

Figure 4:
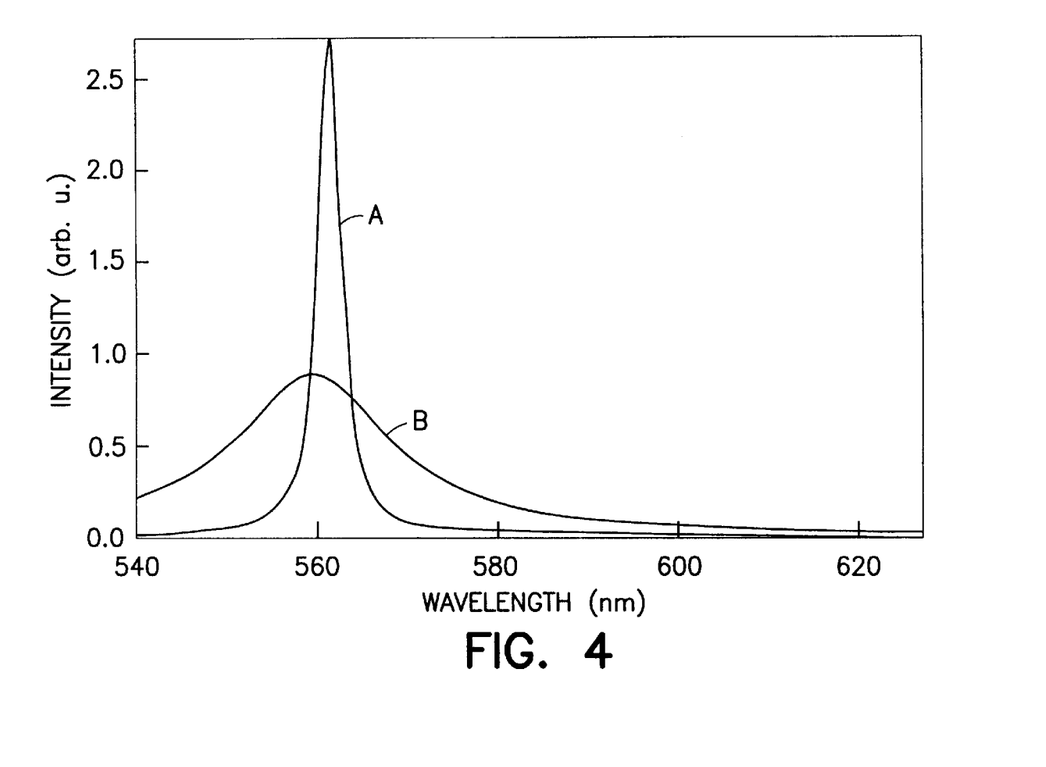
FIG. 4 is a graph that illustrates a difference in optical emission wavelength for the case (A) of a thread containing the gain medium, when the thread is interposed between two scattering layers, and for the case (B) where the thread is isolated from the scattering layers.

FIG. 4 is a graph that illustrates a difference in optical emission wavelength, in response to a laser pump source, for the case of (A) a thread containing a selected dye, when the thread is interposed between the two optical scattering layers of the patch 16 and shirt 14, and for the case (B) where the thread is isolated from the scattering layers. It can be seen for the case where the dye is surrounded by the scattering layers (A) that the emission at about 560 nm is both narrowed and increased in intensity relative to the emission of the dye-containing in isolation. A shift in the emission to longer wavelengths is also observed.

Returning again to FIG. 1, the laser 20 is positioned so as to illuminate the patches 16 as they pass by. The laser 20 can be triggered manually, or triggered by the conveyor 12, or triggered by a photocell or the like that senses when a garment is positioned in an area that is within the beam of the laser 20. In response to illumination with laser light, such as frequency doubled light (i.e., 532 nm) from a (by example) Nd:YAG laser 20, the linear regions 18 each emit their wavelength $\lambda_2$ that is characteristic of the dye or phosphor material that comprises the illuminated regions 18. The emission is scattered and spectrally narrowed, as shown in FIG. 4. The optical detector 22, which may include one or more wavelength selective filters, is used to detect the emission at the wavelength $\lambda_2$. The emission may also be detected visually, assuming that it lies within the visible portion of the spectrum. In either case, the detection of the emission at the characteristic wavelength(s) is decoded by a controller 24 so as to identify the garment 14 and to determine at least its destination. An output of the controller 24 can be connected a diverter 26 used for routing each garment down one of a plurality of paths, such as the two exemplary paths labeled 12a and 12b. In this manner the garments 14 are routed to a predetermined destination and thus sorted.

The patch embodiment depicted in FIG. 2A, having four linear regions 18, when excited by the laser 20 emits a characteristic narrow band emission (e.g., less than about 10 nm) at each of a plurality of wavelengths ($\lambda_2$, $\lambda_3$, $\lambda_4$, $\lambda_5$) if four different dyes are used, or ($\lambda_2$, $\lambda_2$, $\lambda_4$, $\lambda_5$), or ($\lambda_2$, $\lambda_3$, $\lambda_5$), etc. If a "palette" of, by example, seven different dyes are used the patch 16 can emit other wavelength combinations, such as ($\lambda_2$, $\lambda_3$, $\lambda_5$, $\lambda_6$), or ($\lambda_4$, $\lambda_5$, $\lambda_6$, $\lambda_7$), or ($\lambda_2$, $\lambda_3$, $\lambda_5$, $\lambda_8$), etc. The presence of these wavelengths can be detected with the detector 24, in combination with suitable optical passband filters, and subsequently decoded by the controller 24. If an area photodetector is used for the detector 24, such as a CCD, it is also possible to detect a spatial distribution of emission wavelengths, resulting in a further level of information coding/decoding.

The selected dye or dyes (or phosphor(s)) can be provided in fluid form and printed, sprayed, or silk screened onto the surface 16a of the patch 16. A thermo-setting polymer ink, with or without scatterers, can also be employed. It is also within the scope of the invention to coat the regions with a non-index matching polymer.

Although linear regions are shown, any desired pattern can be used, such as discrete solid-colored circles or polygons, concentric circles, serpentine patterns, etc. The resulting indicia, when illuminated by the laser 20, emits the light having wavelengths characteristic of each of the selected dyes. A two layer printing operation can be performed, wherein a bottom layer has a gain medium that emits at $\lambda_2$, and a top layer that has a gain medium that emits at $\lambda_3$. In this manner two distinct optical signatures are emitted after excitation. Also, the lower layer of gain medium can emit at a wavelength that excites and pumps the gain medium of the upper layer.

The indicia can be formed from only the one or more selected dye molecules (and/or phosphors), and the scattering phase can be scattering sites in the surrounding patch 16 and garment 14 (as shown in FIG. 4). Alternatively, or in combination with the scattering provided by the patch/garment, scattering particles, such as $TiO_2$, can be mixed with the selected dye and/or the selected phosphor.

The embodiment of FIG. 3 is preferred, in that the overlying material of the patch 16 also serves to protect the linear regions 18 and to isolate same from the environment.

Although illustrated in the context of hanging garments in FIG. 1, it is also within the scope of this invention to scan and sort garments that are lying flat on a conveyor belt. Other types of textiles can also be sorted in this manner, such as towels, sheets and the like. It is preferred to have relative motion between the textiles and the laser/photodetector, either by transporting the textiles past a stationary laser/photodetector, or vice versa.

Figure 5:
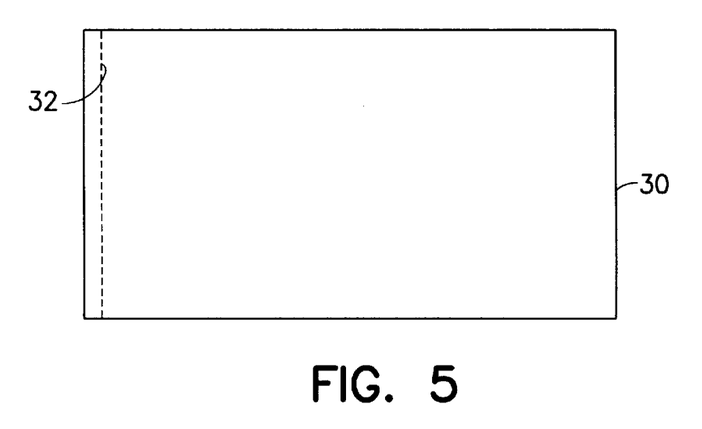
FIG. 5 is a top view of textile that includes light emitting threads in accordance with an embodiment of this invention.

FIG. 5 illustrates a further embodiment of this invention wherein a textile, such as towel 30, is encoded with one or more threads 32. Each thread 32 may be comprised of fibers such as nylon-6, nylon 6/6, PET, ABS, SAN, and PPS. By example, a dye ma y be select ed from Pyrromethene 567, Rhodamine 590 chloride, and Rhodamine 640 perchlorate. The selected dye and scattering particles, such as $TiO_2$, are mixed with a selected textile resin and then extruded. Wet spinning is another suitable technique for forming the fibers. A suitable dye concentration is $2 \times 10^{-3}$M, and a suitable scatterer concentration is approximately $10^{11}/cm^3$. Extrusion at 250° C. followed by cooling in a water bath is one suitable technique for forming the fibers, which may have a diameter of about 50–350 micrometers. A suitable excitation laser threshold fluence is in the range about 5 mJ/cm$^2$ and greater.

Figure 9:
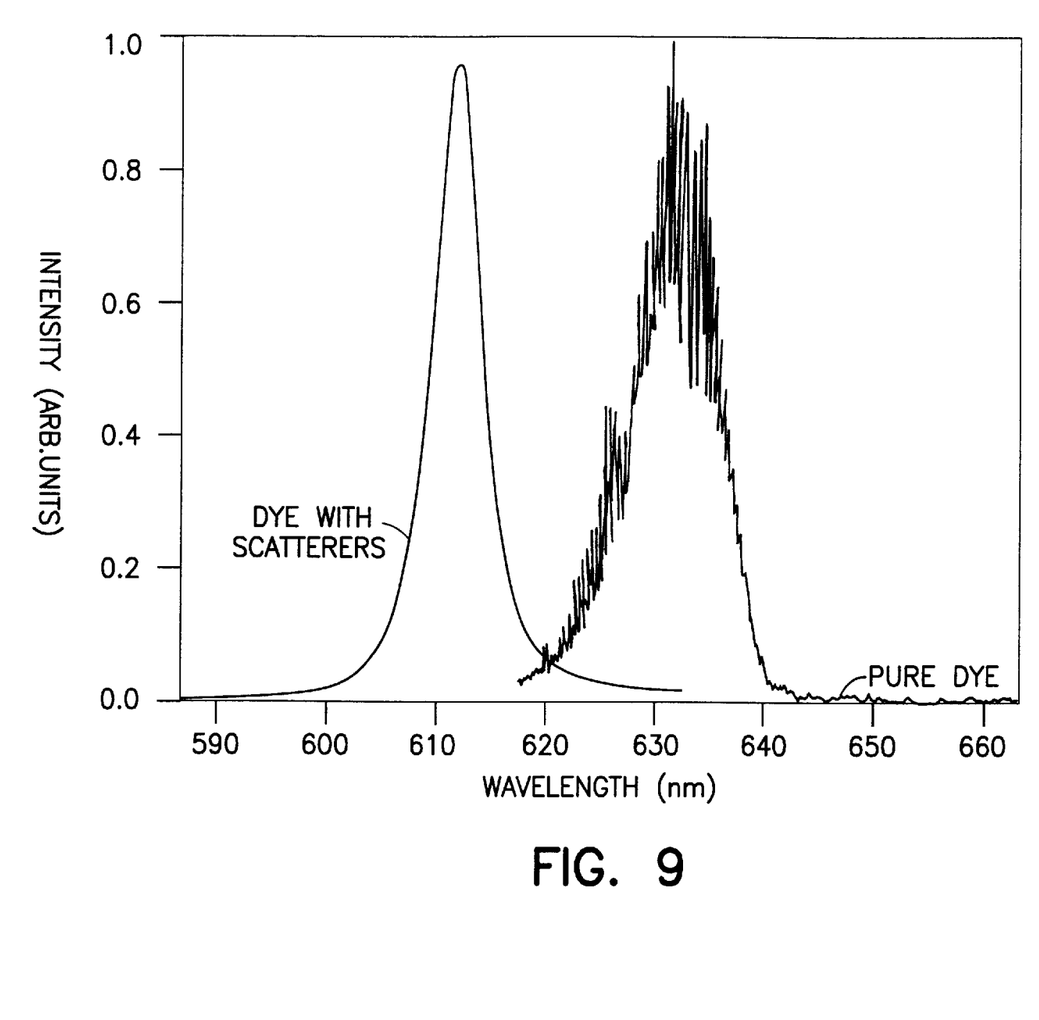
FIG. 9 is a graph that illustrates an emission from nylon-6 fibers containing Rhodamine 640 perchlorate with and without scatterers.

FIG. 9 is a graph that illustrates an emission from nylon-6 fibers containing Rhodamine 640 perchlorate with and without scatterers. The fiber diameter was 200 micrometers in both cases, and the excitation was generated with 5 ns pulses at 532 nm from a Q-switched frequency doubled Nd:YAG laser.

Figure 7:
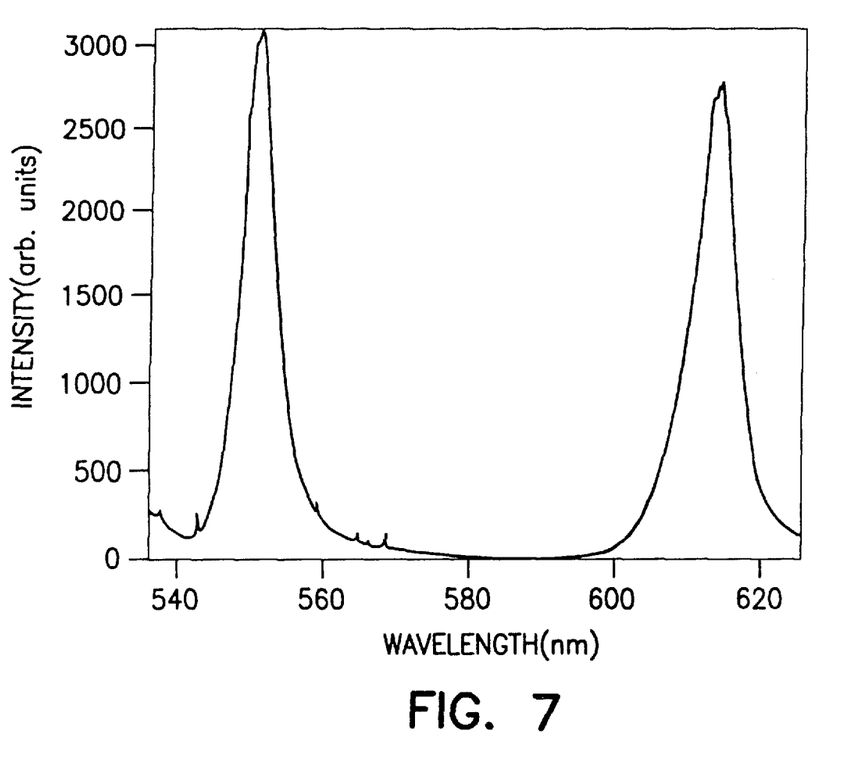
FIG. 7 illustrates the emission from a braided pair of nylon fibers, excited at the 532 nm line of a frequency doubled Nd:YAG laser 20, containing $2 \times 10^{-3}$M Pyrromethene 567 and Rhodamine 640 perchlorate and approximately $10^{11}/cm^3$ $TiO_2$ scatterers, with emission peaks at 552 nm and 615 nm, respectively.

Two or more fibers, each containing a different dye, can be braided together or otherwise connected to provide a composite fiber or thread that exhibits emission at two or more wavelengths. By example, FIG. 7 illustrates the emission from a braided pair of nylon fibers, excited at the 532 nm line of a frequency doubled Nd:YAG laser 20, containing $2 \times 10^{-3}$M Pyrromethene 567 and Rhodamine 640 perchlorate and approximately $10^{11}/cm^3$ $TiO_2$ scatterers, with emission peaks at 552 nm and 615 nm, respectively. By varying the dye-doped fiber types in various combinations of braided or otherwise combined fibers, the resulting composite fibers or threads 32 make it possible to optically encode information into the textile. The characteristic emission lines may be more narrowly spaced that shown in FIG. 7. By example, in that the emission lines of individual ones of the fibers are of the order of 4 nm, one or more further emission wavelengths can be spaced apart at about 6 nm intervals.

It is also within the scope of the invention to provide a single fiber with two dyes, where the emission from one dye is used to excite the other dye, and wherein only the emission from the second dye may be visible.

In one embodiment Rhodamine 640 is excited at 532 nm. The Rhodamine 640 emits 620 nm radiation with is absorbed by Nile Blue, which in turn emits at 700 nm.

Figure 13:
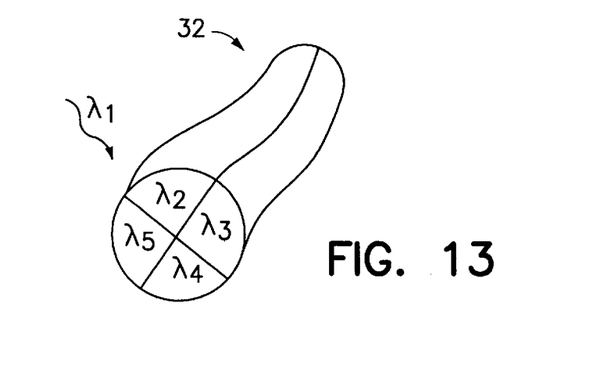
FIG. 13 is an end view of a sectored thread in accordance with an embodiment of this invention.

It is also within the scope of this invention to provide a sectored thread 32, as shown in FIG. 13, having different regions or sectors each containing a different dye or phosphor, Such a thread can be formed by using multiple extrusion heads, each extruding a different polymer/dye combination, that are subsequently joined together. More or less than four sectors can be used. When excited anywhere along its length with pump light $\lambda_1$ the sectored thread 32 emits with a plurality of characteristic wavelengths, such as the wavelengths ($\lambda_2, \lambda_3, \lambda_4, \lambda_5$). In this embodiment a single thread 32 can encode multiple items of information regarding the textile with which it is associated.

During use a selected thread or threads 32 can be simply stitched into the textile at one or more predetermined locations, and their emission wavelength(s) subsequently detected as described above. The threads 32 can also be stitched into the patch 16, and thus applied to the textile when the patch 16 is applied. The emission wavelength or wavelengths are selected so as to encode the desired information, such as a customer identification, a date the textile was first placed into service, an identification of the vendor of the textile, an identification of the type and/or size of the textile, etc.

By example, if N is the total number or set of fibers each of which is capable emitting at a distinct and resolvable wavelength, and if a subset of X fibers are selected, it can be shown that there are $(N!)/((N-x)!*x!)$ possible wavelength combinations. By example, a set of 20 fibers can encode over $10^6$ items ($2^N-1$)

The use of this invention enables a wide variety of garments and textiles to be encoded and subsequently automatically separated from one another. By example, different sized tablecloths can each be identified by having unique optical coding, as can different size (and color) napkins, and different types of aprons, towels, sheets, and garments (e.g., a chef's coat can be encoded differently than a laboratory apron, and subsequently automatically separated either before or after washing).

Consider the case of up to three threads 32 disposed in a garment label or at the border of a linen. Each thread 32, when excited, emits a precise wavelength. Each wavelength, when detected, can be considered as a bit. In this case there are three bits: A, B, and C. These three bits can thus be combined to yield seven unique combinations: A, B, C, AB, AC, BC, ABC. In this embodiment the ordering of the bits is not important (i.e., ABC=CBA), unlike a bar code, and the need for scanning is eliminated. If the sectored thread 32 of FIG. 13 is used, then it is possible to replace the three threads with a single thread having different wavelength combinations.

Figure 10:
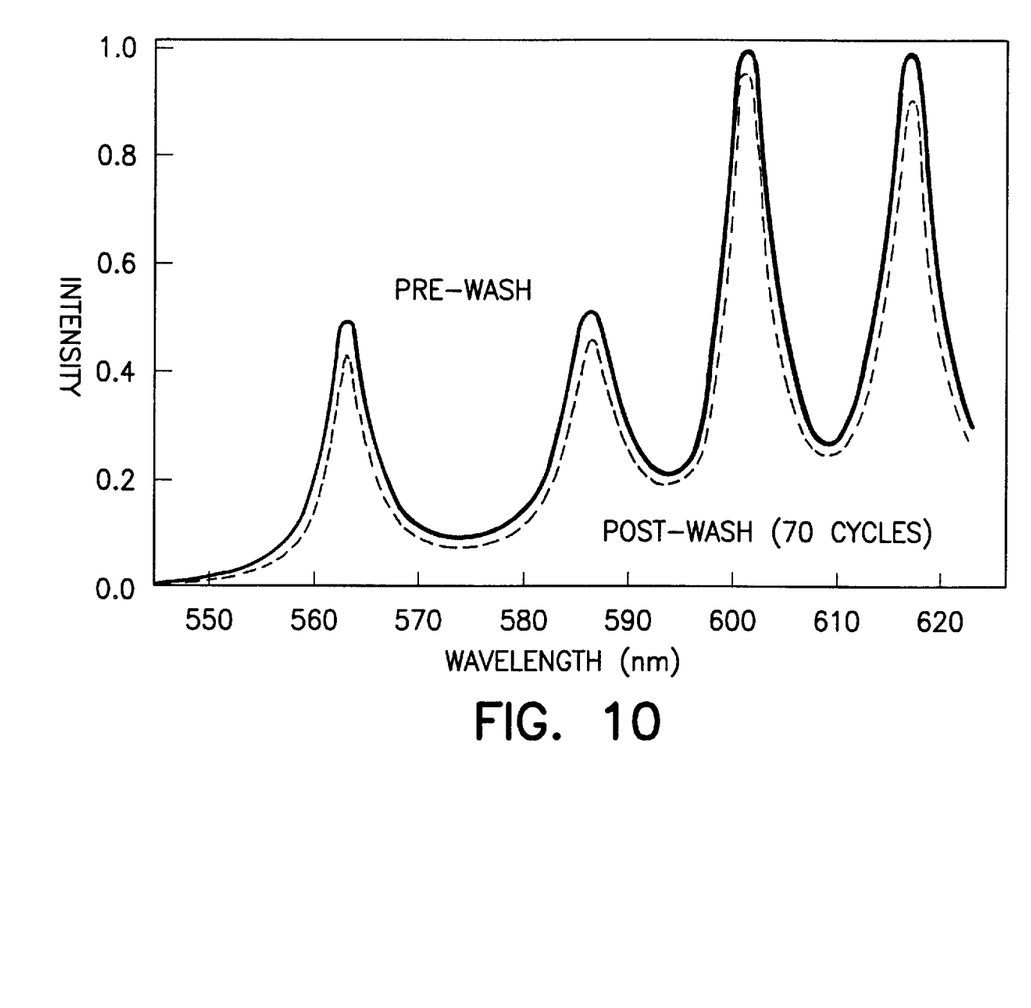
FIG. 10 illustrates an effect of 70 wash cycles on the intensity of the emission of threads fabricated and used in accordance with this invention.

FIG. 10 illustrates an effect of 70 wash cycles on the intensity of the emission of threads fabricated and used in accordance with this invention. In the illustrated example a textile has three threads that emit at about 563 nm, 587 nm, 602 nm, and 615 nm. It can be seen that the effect of seventy wash cycles reduces the intensity of the emission by only a few per cent.

Figure 8:
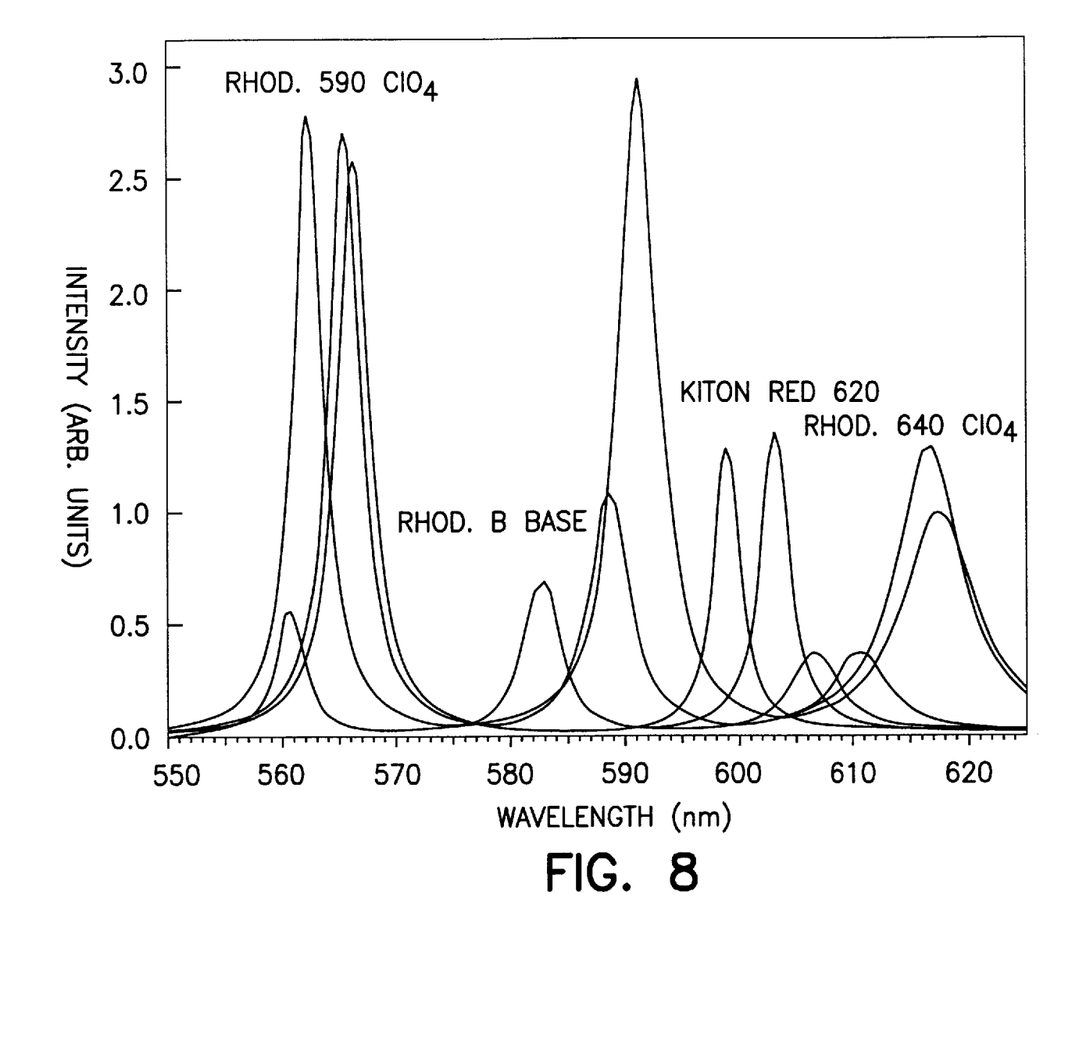
FIG. 8 is a graph that illustrates a wavelength tuning effect that can be achieved by varying the diameter of fibers that form the threads of FIG. 5.

It is also within the scope of this invention to vary the diameter of the individual fibers to achieve a wavelength tuning. Referring to FIG. 8, it is shown that an emission peak for a selected dye can be shifted by some tens of nanometers by varying the diameter of the fibers that comprise the thread 32. By example, it has been found that a given fiber having a diameter of 100 micrometers will emit a shorter wavelength than a fiber, containing the same dye (and scattering concentration), having a thickness of 250 micrometers. See, for example, the various emission peaks associated with Kiton Red 620, each of which is obtained from a fiber having a different diameter.

It has also been found that the emission wavelength can be shifted by varying the concentration of scattering particles.

The embodiment shown in FIG. 5 can also employ the scattering obtained from the textile adjacent to or surrounding the threads 32, either to enhance the scattering provided by scattering particles included in the fibers that comprise the threads, or in place of scattering particles.

Figure 11:
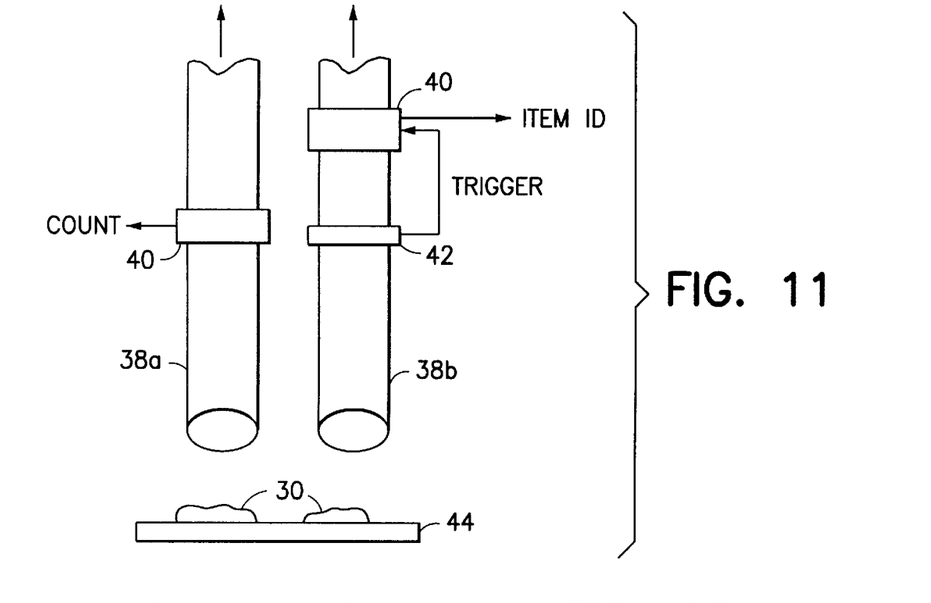
FIG. 11 is a simplified view of a portion of a vacuum-based garment and linen handling and transport system in accordance with an aspect of this invention.

FIG. 11 illustrates an embodiment of this invention wherein a plurality of conduits 38a, 38b are provided for conveying textiles to different locations. Although two conduits are shown, any number can be used. In this embodiment a vacuum system (not shown) is used to draw the textiles through the conduits in the direction indicated by the arrows. A terminal end of each conduit 38 may be positioned adjacent to a sorting table 44 where a worker manually sorts different types of textiles 30, such as soiled textiles returned from a user, and inserts the textiles into the appropriate conduit 38a, 38b. By example, soiled wash cloths are inserted into conduit 38a, and soiled towels into conduit 38b.

In accordance with this invention an optical unit 40 is placed within each conduit. The optical unit 40 includes a laser source and one or more wavelength selective detectors, similar to the embodiment shown in FIG. 1. As the textile passes through the laser beam the portion of the textile that contains the patch 16 and/or thread(s) 32 emits its characteristic wavelength(s), which are detected. In the case of conduit 38a the output of the optical unit 40 is used simply as an indication of the presence of a textile, and an thus be used to count the number of textiles that pass through the conduit. In the prior art it is known to use a simple beam-interrupting emitter/photodetector for this purpose.

In the conduit 38b such a conventional beam-interrupting emitter/photodetector unit 42 is used to generate a trigger signal to pulse the laser within the optical unit 40, which then outputs an indication of the information encoded into the textile in accordance with this invention. By example, the item ID can be output from the optical unit 40 as a quality assurance check that the manual sorting procedure has been correctly performed.

In some embodiments it may be desirable to locate the laser at a remote location, and to provide the laser emission ($\lambda_1$) to each conduit through an optical fiber.

Figure 12:
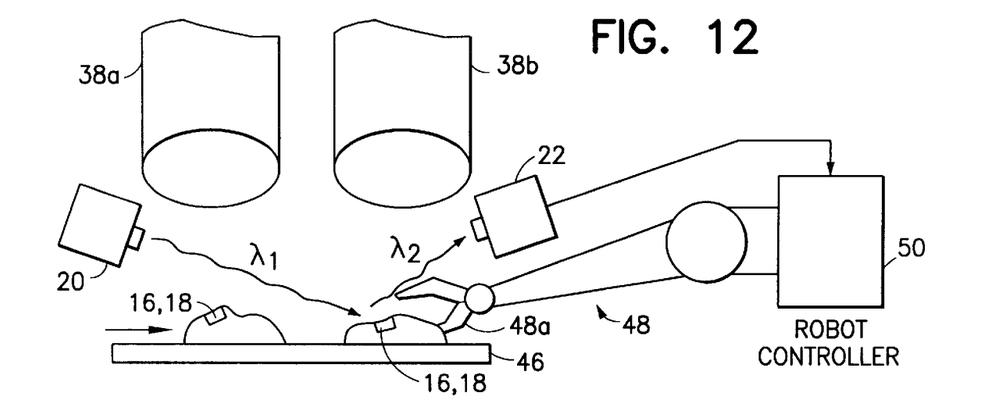
FIG. 12 is a simplified view of a further portion of the vacuum-based garment and linen handling and transport system in accordance with a further aspect of this invention.

FIG. 12 illustrates an embodiment of this invention wherein a multiple degree of freedom robot arm 48 and robot arm controller 50 are used to automate the sorting process. In this embodiment a conveyor 46 moves the textiles in the direction shown by the arrow. As each textile passes through the laser beam from the laser 20 the portion of the textile that contains the patch 16 and/or thread(s) 32 emits its characteristic wavelength(s), which are detected by the photodetector 22. The output of the photodetector 22 is input to the robot controller 50, which can then identify the type of textile and cause the end effector 48a of the robot arm 48 to grasp the textile and place it into the appropriate conduit 38.

While described in the context of moving rails, conveyors, conveyor belts, and conduits for transporting textiles before and/or after exposure to the pump radiation, it should be realized that any suitable apparatus for moving textiles and garments can be employed. By example, in the embodiment of FIGS. 11 and 12 the conduits 38 could pass from one floor of a building to a lower floor, and the textiles could simply be dropped into the appropriate conduit. In this case as the textile falls past the optical unit 40 the information encoded into textile can be read. This embodiment thus eliminates the need for a vacuum system. If desired, a single conduit could be used which leads into branching conduits.

The output of the photodetector can then be used to activate some suitable type of diverting mechanism, such as an air blast, to direct a falling textile into an appropriate branching conduit. In this case it is not necessary to manually sort the textiles prior to placing then into the conduit, as the textiles are sorted as they fall.

Thus, while the invention has been particularly shown and described with respect to preferred embodiments thereof, it will be understood by those skilled in the art that changes in form and details may be made therein without departing from the scope and spirit of the invention.

What is claimed is:

1. A method for sorting textiles, comprising the steps of:
    providing a plurality of textiles to be sorted, each of the textiles comprising a portion that includes an electromagnetic radiation emitting and amplifying material;
    for each textile, illuminating at least the portion with laser light that exceeds a threshold fluence;
    detecting a narrow band laser-like emission of at least one wavelength from the portion in response to the step of illuminating; and
    sorting the textiles based on the detected laser-like emission.

2. A method as in claim 1, wherein step of providing a textile provides a textile having at least one stitched-in thread, the thread comprising a substrate material and the electromagmetic radiation emitting and amplifying material in combination with scatterers for providing the laser-like emission in response to the step of illuminating.

3. A method as in claim 2, wherein the scatterers comprise the material of the textile either alone or in combination with scattering particles added to the thread.

4. A method as in claim 2, wherein the scatterers comprise the material of the textile either alone or in combination with the material of the patch.

5. A method as in claim 1, wherein step of providing a textile provides a textile having an applied patch containing the electromagnetic radiation emitting and amplifying material in combination with scatterers for providing the laser-like emission in response to the step of illuminating.

6. A method as in claim 5, wherein the patch is applied such that the electromagnetic radiation emitting and amplifying material is interposed between an exposed surface of the patch and a surface of the textile.

7. A method as in claim 1, wherein step of providing a textile provides a textile having at least one stitched-in thread, the thread comprising a substrate material and the electromagnetic radiation emitting and amplifying material in combination with scatterers for providing the laser-like emission, in response to the step of illuminating, said at least one thread being comprised of N filaments individual ones of which comprise a substrate material and the electromagnetic radiation emitting and amplifying material in combination with scatterers for providing the laser-like emission in response to the step of illuminating, wherein said at least one thread emits light at N distinguishable wavelengths.

8. A method as in claim 1, wherein the electromagnetic radiation emitting and amplifying material is comprised of at least one of a dye or a phosphor.

9. A patch capable of being affixed to a surface of a textile, comprising:
    a substrate having first and second major surfaces; and
    disposed on said first major surface, an electromagnetic radiation emitting and amplifying material in combination with scatterers that are one of added to the material or that are provided at least in part by said substrate for providing a laser-like emission in response to illumination with laser light, said electromagnetic radiation emitting and amplifying material encoding information regarding said textile.

10. A patch as in claim 9, wherein said patch includes at least one thread, the thread comprising a substrate material and the electromagnetic radiation emitting and amplifying material in combination with scatterers for providing the laser-like emission.

11. A patch as in claim 10, wherein the scatterers comprise the material of the patch substrate either alone or in combination with scattering particles added to the thread.

12. A patch as in claim 10, wherein there is relationship between thread diameter and emission wavelength, and wherein an emission wavelength of the at least one thread is selected at least in part by a diameter of said thread.

13. A patch as in claim 9, wherein said patch includes at least one region comprised of a dye or a phosphor applied to said surface.

14. A patch as in claim 9, wherein the patch is applied such that the electromagnetic radiation emitting and amplifying material is interposed between said second major surface of said substrate and the surface of the textile.

15. A textile, comprising at least one stitched-in thread, the thread comprising a substrate material and an electromagnetic radiation emitting and amplifying material in combination with scatterers for providing a laser-like emission in response to illumination with a laser, said electromagnetic radiation emitting and amplifying material encoding information regarding said textile.

16. A textile as in claim 15, wherein said at least one thread is comprised of N filaments individual ones of which comprise a substrate material and the electromagnetic radiation emitting and amplifying material in combination with scatterers for providing the laser-like emission, wherein said at least one thread emits light at N distinguishable wavelengths.

17. A textile as in claim 15, wherein said at least one thread is a sectored thread.

18. Apparatus for sorting textiles, comprising:
    a laser generating a beam for illuminating at least a portion of the textiles with laser light that exceeds a threshold fluence;
    means for moving the textiles relative to the laser beam, each of the textiles comprising a portion that includes an electromagnetic radiation emitting and amplifying material;
    an optical detector for detecting a laser-like emission of at least one wavelength from the portion in response to the laser beam illuminating the portion; and
    means for directing the textiles to predetermined locations in accordance with the detected laser-like emission.

19. Apparatus as in claim 18, wherein each textile includes a patch affixed to a surface of the textile, said patch comprising:
    a substrate having first and second major surfaces; and
    disposed on said first major surface, the electromagnetic radiation emitting and amplifying material in combination with scatterers that are one of added to the material or that are provided at least in part by said substrate and said textile for providing a laser-like emission in response to illumination by said laser, said electromagnetic radiation emitting and amplifying material encoding information regarding said textile.

20. Apparatus as in claim 19, where said patch includes at least one thread, the thread comprising a substrate material and the electromagnetic radiation emitting and amplifying material in combination with scatterers for providing the laser-like emission.

21. Apparatus as in claim 20, wherein the scatterers comprise the material of the patch substrate either alone or in combination with scattering particles added to the thread.

22. Apparatus patch as in claim 19, wherein said patch includes at least one region comprised of a dye or a phosphor applied to said first major surface.

23. Apparatus as in claim 19, wherein said patch is applied such that the electromagnetic radiation emitting and amplifying material is interposed between said second major surface of said substrate and the surface of the textile.

24. Apparatus as in claim 20, wherein there is relationship between thread diameter and emission wavelength, and wherein an emission wavelength of the at least one thread is selected at least in part by a diameter of said thread.

25. Apparatus as in claim 20, wherein said at least one thread is comprised of N filaments individual ones of which comprise a substrate material and the electromagnetic radiation emitting and amplifying material in combination with scatterers for providing the laser-like emission, wherein said at least one thread emits light at N distinguishable wavelengths.

26. Apparatus as in claim 18, wherein said textile includes at least one thread, the thread comprising a substrate material and the electromagnetic radiation emitting and amplifying material in combination with scatterers for providing the laser-like emission.

27. A method for sorting substantially identical objects, comprising the steps of:
providing a plurality of objects to be sorted, each of the objects comprising a portion that includes an electromagnetic radiation emitting and amplifying material;
for each object, illuminating at least the portion with laser light that exceeds a threshold fluence;
detecting a narrow band laser-like emission of at least one wavelength from the portion in response to the step of illuminating; and
sorting the objects based on the detected laser-like emission.

28. A method as in claim 27, wherein step of providing an object provides an object having at least one filament, the filament comprising a substrate material and the electromagnetic radiation emitting and amplifying material in combination with scatterers for providing the laser-like emission in response to the step of illuminating.

29. A method as in claim 28, wherein the scatterers comprise the material of the object either alone or in combination with scattering particles added to the filament.

30. A method as in claim 27, wherein step of providing an object provides an object having an applied coating containing the electromagnetic radiation emitting and amplifying material in combination with scatterers for providing the laser-like emission in response to the step of illuminating.

31. A method as in claim 27, wherein step of providing an object provides an object having a plurality of N filaments individual ones of which comprise a substrate material and the electromagnetic radiation emitting and amplifying material in combination with scatterers for providing the laser-like emission in response to the step of illuminating, wherein said at least one filament emits light at N distinguishable wavelengths.

32. A method as in claim 27, wherein the portion that includes an electromagnetic radiation emitting and amplifying material is isolated from the environment.

33. A method as in claim 27, wherein the electromagnetic radiation emitting and amplifying material is comprised of at least one of a dye or a phosphor.

34. An object, said object comprising at least one filament, said at least one filament comprising a substrate material and at least one electromagnetic radiation emitting and amplifying material in combination with scatterers for providing a laser-like emission in response to illumination with a laser, said electromagnetic radiation emitting and amplifying material encoding information regarding said object.

35. An object as in claim 34, wherein said at least one filament is comprised of N sub-filaments individual ones of which comprise a substrate material and the electromagnetic radiation emitting and amplifying material in combination with scatterers for providing the laser-like emission, wherein said at least one filament emits light at N distinguishable wavelengths.

36. An object as in claim 34, wherein said at least one filament is a sectored filament comprised of N filament regions that extend along a length of said filament, individual ones of said filament regions comprise a substrate material and the electromagnetic radiation emitting and amplifying material in combination with scatterers for providing the laser-like emission, wherein said at least one filament emits light at N distinguishable wavelengths.

37. An object as in claim 34, and further comprising means for isolating said at least one filament from the environment.

38. An object, said object comprising a plurality of coatings, each of said coatings comprising at least one electromagnetic radiation emitting and amplifying material in combination with scatterers for providing a laser-like emission in response to illumination with a laser, said electromagnetic radiation emitting and amplifying material encoding information regarding said object.

39. An object as in claim 38, and further comprising means for isolating said plurality of coatings from the environment.

40. A method for identifying objects, comprising the steps of:
providing a plurality of objects to be identified, each of the objects comprising a portion that includes an electromagnetic radiation emitting and amplifying material;
for each object, illuminating at least the portion with laser light that exceeds a threshold fluence;
detecting a narrow band laser-like emission of at least one wavelength from the portion in response to the step of illuminating; and
identifying the objects based on the detected laser-like emission.

41. A method as in claim 40, wherein step of providing an object provides an object having at least one filament, the filament comprising a substrate material and the electromagnetic radiation emitting and amplifying material in combination with scatterers for providing the laser-like emission in response to the step of illuminating.

42. A method as in claim 41, wherein the scatterers comprise the material of the object either alone or in combination with scattering particles added to the filament.

43. A method as in claim 40, wherein step of providing an object provides an object having an applied coating containing the electromagnetic radiation emitting and amplifying material in combination with scatterers for providing the laser-like emission in response to the step of illuminating.

44. A method as in claim 40, wherein step of providing an object provides an object having a plurality of N filaments individual ones of which comprise a substrate material and the electromagnetic radiation emitting and amplifying material in combination with scatterers for providing the laser-like emission in response to the step of illuminating, wherein said at least one filament emits light at N distinguishable wavelengths.

45. A method as in claim 40, wherein the portion that includes an electromagnetic radiation emitting and amplifying material is isolated from the environment.

46. A method as in claim 40, wherein the electromagnetic radiation emitting and amplifying material is comprised of at least one of a dye or a phosphor.

47. A method for sorting garments, comprising the steps of:

providing a plurality of garments to be sorted, each of the garments comprising a portion that includes an electromagnetic radiation emitting and amplifying material;

for each garment in turn, illuminating at least the portion with laser light that exceeds a threshold fluence;

detecting a narrow band laser-like emission of at least one wavelength from the portion in response to the step of illuminating; and sorting the garments based on the detected laser-like emission.

* * * * *